United States Patent
Polishook et al.

(10) Patent No.: US 10,412,965 B2
(45) Date of Patent: Sep. 17, 2019

(54) USE OF THE ANTIFUNGAL ILICICOLIN H IN AGRICULTURE

(71) Applicant: AGROBIOLOGICS, LLC, Rehoboth Beach, DE (US)

(72) Inventors: Jon D. Polishook, Old Bridge, NJ (US); Daniel P. Ring, Doylestown, PA (US); Sheo B. Singh, Edison, NJ (US); James Frederic Walter, Furlong, PA (US)

(73) Assignee: Agrobiologics LLC, Rehoboth Beach, DE (US)

( * ) Notice: Subject to any disclaimer, the term of this patent is extended or adjusted under 35 U.S.C. 154(b) by 0 days.

(21) Appl. No.: 15/763,569

(22) PCT Filed: Oct. 28, 2016

(86) PCT No.: PCT/US2016/059569
§ 371 (c)(1),
(2) Date: Mar. 27, 2018

(87) PCT Pub. No.: WO2017/075527
PCT Pub. Date: May 4, 2017

(65) Prior Publication Data
US 2018/0271092 A1 Sep. 27, 2018

Related U.S. Application Data

(60) Provisional application No. 62/248,371, filed on Oct. 30, 2015.

(51) Int. Cl.
*A01N 43/40* (2006.01)
*A01N 25/04* (2006.01)

(52) U.S. Cl.
CPC .............. *A01N 43/40* (2013.01); *A01N 25/04* (2013.01); *A01N 2300/00* (2013.01)

(58) Field of Classification Search
CPC ..... A01N 43/00; A01N 25/04; A01N 2300/00
See application file for complete search history.

(56) References Cited

U.S. PATENT DOCUMENTS

| 8,282,950 B2 * | 10/2012 | Bohus | A01N 25/04 424/405 |
| 9,944,607 B2 * | 4/2018 | Vincent | C07D 233/86 |
| 2015/0208656 A1 | 7/2015 | Grammenos et al. | |

OTHER PUBLICATIONS

Brandt et al. (Emerging infectious disease, V19(10); 2013.*
Singh et al., Antifungal Spectrum, In Vivo Efficacy, and Structure-Activity Relationship of Ilicicolin H, ACS Medicinal Chemistry Letters, vol. 3, No. 10, Sep. 7, 2012.
Hayakawa et al., The Ilicicolins, Antibiotics from Cylindrocladium Ilicicola, The Journal of Antibiotics, vol. 24, No. 9, 1971.
International Search Report in PCT/US2016/059569, International Filing Date Oct. 28, 2016.
European Patent Office Search Report in EP Application No. 16861001.2 dated Apr. 12, 2019.
Singh, Sheo B. et al: "Antifungal Spectrum, In Vivo Efficacy, and Structure-Activity Relationship of Ilicicolin H", ACS Medicinal Chemistry Letters, vol. 2, No. 10, Sep. 7, 2012.
Gognies, Sabine, et al: "*Saccharomyces cerevisiae*, a potential pathogen towards grapevine, *Vitis vinifera*", Fems Microbiology Ecology, vol. 37, No. 2, Oct. 1, 2001.
Gutierrez-Cirlos, Emma Berta et al: "Inhibition of the Yeast Cytochrome bc 1 Complex by Ilicicolin H, a Novel Inhibitor That Acts at the Qn Site of the bc 1 Complex", Journal of Biological Chemistry, vol. 279, No. 10, Mar. 5, 2004.

* cited by examiner

*Primary Examiner* — Shirley V Gembeh
(74) *Attorney, Agent, or Firm* — White and Williams LLP

(57) ABSTRACT

The present invention is concerned with the use of the natural product Ilicicolin H as an agricultural fungicide, compositions comprising Ilicicolin H, and the use of such compositions to treat, control or prevent fungal infection in agricultural products.

4 Claims, No Drawings

USE OF THE ANTIFUNGAL ILICICOLIN H IN AGRICULTURE

PRIORITY

This application is a National Stage of International Application number PCT/US16/59569, filed Oct. 28, 2016, which claims the benefit of U.S. Provisional Application No. 62/248,371, filed Oct. 30, 2015, the disclosures of which are incorporated herein by reference.

FIELD OF THE INVENTION

The present invention is concerned with the use of the natural product Ilicicolin H as an agricultural fungicide. The invention is also concerned with compositions comprising Ilicicolin H, their preparation, and methods of using such compositions to control agricultural pests including, but not limited to, fungi selected from the group consisting of *Botryotinia fuckeliana, Glomerella lagenarium, Mycosphaerella arachidis, Zymoseptoria tritici, Gaeumannomyces graminis, Monographella nivalis, Thanatephorus cucumeris, Sclerotinia sclerotiorum,* and *Puccinia recondita*.

BACKGROUND OF THE INVENTION

In the agricultural industry there is a need to control plant pathogens that would otherwise destroy crops and reduce yields. Farmers have traditionally employed a variety of methodologies to control these pests, one of which has been the use of compounds with antimicrobial activity, called fungicides, to protect the plants and prevent crop damage. There are many types of plant diseases, and foreign microorganisms can be introduced into new areas causing disease outbreaks. Current fungicides have traditionally been chemically synthesized compounds that have limited spectrum of activity and often require repeated usage creating a cause for environmental concern. These concerns include contamination of foodstuffs, soil, surface and ground water and their impact on native microbial and insect populations. In addition, pathogens have been able to develop resistance to conventional fungicides, and as a result the industry is consistently searching for new chemical compounds with new modes of action to combat disease resistance.

Ilicicolin H is one of several natural secondary metabolites made by imperfect fungi. These metabolites generally act as protectants for the fungus. Ilicicolin H is produced by strains of *Cylindrocladium iliciola* (Hayakawa et al., "Ilicicolins, antibiotics from *Cylindrocladium ilicicola*", *Journal of Antibiotics* 1971, 24, 653-4) and *Fusarium* sp. (Shao et al., "Metabolites of endophytic fungus *Fusarium* from *Spartina alterniflora*", *Zhongguo Tianran Yaowu* 2007, 5, 108-111), and *Gliocladium roseum* (Junker et al., "Scale-Up Studies on a Defined Medium Process for Pilot Plant Production of Ilicicolin by *Gliocladium roseum*," *Biotechnology Progress* 2001, 17, 278-286).

Ilicicolin H is an antibiotic that was first identified to have activity against the human pathogen *Candida albicans* and was investigated for use in the treatment of complications to HIV infection in humans (Guetierrez-Cirlos et al., "Inhibition of the Yeast Cytochrome bcl Complex by Ilicicolin H, a Novel Inhibitor That Acts at the Qn Site of the bclComplex," *Journal of Biological Chemistry* 2004, 279, 8708-8714). Ilicicolin H whose structure is shown below is a 5-(4-hydroxyphenyl)-2-pyridone with a bicyclic decalin system. The compound inhibits the mitochondrial respiration of certain fungi by inhibiting the cytochrome bcl complex. Ilicicolin H has low cyctotoxity (HeLa cells, $ED_{50}$=2 ug/ml) and low acute toxicity in mice (Hayakawa et al., "Ilicicolins, antibiotics from *Cylindrocladium ilicicola*," *Journal of Antibiotics* 1971, 24, 653-4). However, Ilicicolin H has not previously been shown to be active against plant pathogenic fungi.

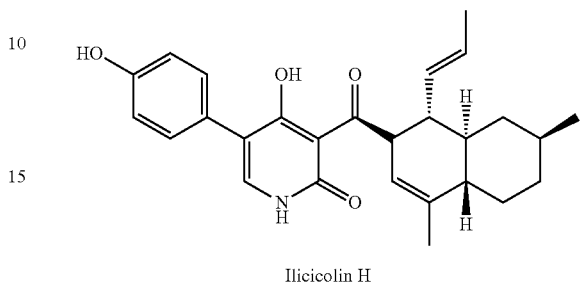

Ilicicolin H

It has now been found that Ilicicolin H is useful as an agricultural fungicide to treat, prevent, or control fungal infections in agricultural products, such as plants and seeds.

One aspect of the present invention is concerned with agricultural compositions of Ilicicolin H comprising an effective amount of the antifungal compound and an agriculturally acceptable carrier. Such compositions may additionally comprise one or more excipients selected from the group consisting of (a) one or more diluents, (b) one or more binders or binding agents, (c) one or more dispersing agents, (d) one or more emulsifying agents, (e) one or more surfactants or wetting agents, (f) one or more sticking agents, (g) one or more thickening agents, and (h) a pH adjuster. In one embodiment the surfactant is an anionic surfactant. In a second embodiment the surfactant is a non-ionic surfactant.

Ilicicolin H and agricultural compositions of Ilicicolin H of the present invention may also be used in combination with one or more other agents useful to treat, prevent, or control agricultural pests in the field. In such combinations the compositions of the present invention and other active agents may be administered separately or in conjunction. In addition, the administration of one element may be prior to, concurrent to, or subsequent to the administration of the other agent(s).

Examples of other active ingredients that may be administered in combination with compositions of the present invention, and either administered separately or in the same agricultural composition, include, but are not limited to:

(1) antifungal agents, such as azoxystrobin and myclobutanil;

(2) plant growth regulators, such as dikegulac-sodium and trinexapac-ethyl;

(3) herbicides, such as prodiamine and glyphosate;

(4) insecticides, such as bifenthrin and malathion; and (5) acaricides, such as avermectin and kelthane.

The agricultural compositions of the present invention may contain about 0.1 to 95 percent by weight Ilicicolin H.

It is another aspect of the present invention to provide methods of treating, controlling, or preventing fungal infections on an agricultural product comprising applying to the agricultural product or plant the present agricultural compositions of Ilicicolin H. The compositions of the present invention may be applied using a variety of methodologies, including soil drench, seed treatment, granular and foliar spray. With regard to the treatment of seeds, the compositions may alternatively be applied directly to the seed before planting of the seed or applied to the locus or soil in which the seeds are sown prior to the planting of the seed.

In such methods of the present invention the concentration of Ilicicolin H to be applied to the agricultural product is about 0.001 to 1 percent by weight. In a class of this method the concentration of Ilicicolin H to be applied to the agricultural product is about 0.001 to 0.01 percent by weight.

Another aspect of the present invention relates to the total amount of Ilicicolin H to be applied per area of the field. In one class of this aspect about 2 to about 1000 grams of Ilicicolin H are to be applied per acre. In a subclass of this class about 5 to 500 grams of Ilicicolin H are to be applied per acre. In a second class of this aspect about 0.025 kilograms to about 5 kilograms of Ilicicolin H are to be applied per hectare. In a subclass of this second class about 0.05 kilograms to about 1 kilogram of Ilicicolin H are to be applied per hectare.

Another aspect of the present invention relates to the use of Ilicicolin H and the compositions of the present invention to treat, control, or prevent fungal infections on an agricultural product.

It is another aspect of the present invention to provide for the use of Ilicicolin H in the manufacture of a composition for use in treating, controlling, or preventing a fungal infection on an agricultural product.

The present invention also relates to a food, feed, or agricultural product treated with a composition of the present invention.

The present invention also relates to a process for the treatment of an agricultural product which comprises applying a composition of the present invention to such agricultural product or plant.

The present invention also relates to the use of a fermentation broth derived from strains of *Cylindrocladium ilicicola* and *Gliocladium roseum* as a live cell or cell suspension to treat, control, or prevent a fungal infection on an agricultural product. Such fermentation broths contain the antifungal agent Ilicicolin H which need not be isolated, purified, and re-formulated for use as an agricultural fungicide.

These and other aspects will become readily apparent from the detailed description of the invention which follows.

DETAILED DESCRIPTION OF THE INVENTION

The present invention is concerned with the use of the naturally occurring antifungal Ilicicolin H to control the growth of agricultural pests including, but not limited to, *Botryotinia fuckeliana, Glomerella lagenarium, Mycosphaerella arachidis, Zymoseptoria tritici, Gaeumannomyces graminis, Monographella nivalis, Thanatephorus cucumeris, Sclerotinia sclerotiorum,* and *Puccinia*. Ilicicolin H can be used to control a variety of plant diseases and can be applied in a variety of methodologies, including soil drench, seed treatment, granular and foliar spray. It can be readily formulated into a variety of compositions, including, but not limited to, emulsifiable concentrates, inverse emulsions, microemulsions, dispersible granules, wettable powders, dusts, and granules.

Ilicicolin H offers several advantages over existing synthetic fungicides. Since it is derived from natural sources, it already occurs in the environment and biological processes to degrade the compound are already present in the environment. Unlike many conventional fungicides, Ilicicolin H does not contain any heavy metals or halogens and therefore is totally biologically degradable. Moreover, Ilicicolin H has a different mechanism of action from existing commercial fungicides and therefore can be used to reduce fungicide resistance found in certain plant diseases.

The term "agricultural product" as used herein is to be understood in a very broad sense and includes, but is not limited to, cereals, e.g., wheat, barley, rye, oats, rice, sorghum, and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, and soybeans; oleaginous plants, e.g. rape, mustard, poppy, olive, sunflower, coconut, castor-oil plant, cocoa, and ground-nuts; cucurbitaceae, e.g. pumpkins, gherkins, melons, cucumbers, squashes, and aubergines; fibrous plants, e.g. cotton, flax, hemp, and jute; citrus fruit, e.g. oranges, lemons, grapefruits, mandarins, and limes; tropical fruit, e.g. papayas, passion fruit, mangos, carambolas, pineapples, bananas, and kiwis; vegetables, e,g. spinach, lettuce, asparagus; brassicaceae, such as cabbage and turnips, carrots, onions, tomatoes, potatoes, seed potatoes, hot and sweet peppers; laurel-like plants, e.g. avocado, cinnamon, camphor tree; or products, such as maize, tobacco, nuts, coffee, sugarcane, tea, grapevines, hops, rubber plants, as well as ornamental plants, e.g. cut flowers, roses, tulips, lilies, Narcissus, crocuses, hyacinths, dahlias, Gerbia, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

The following Examples are provided to illustrate the invention and are not intended to be construed as limiting the scope of the invention in any manner.

EXAMPLE 1

Ilicicolin H was evaluated in mycelial growth tests in artificial media against *Pythium dissimile, Alternaria solani, Botryotinia fuckeliana,* and *Gibberella zeae* at rates of 20 parts per million (ppm). Mycelial growth or disease inhibition was assessed visually and scored using a 3 band system (0, 55, and 99 where 99=total inhibition of hyphal growth/disease development, 55=partial inhibition, 0=no inhibition), 4 to 14 days after inoculation depending on the assay. Scores are given for numbered replicates, and average scores for the replicates (avg). Results are presented in Table 1 below. Ilicicolin H was active against *Botryotinia fuckeliana* but not active against *Pythium dissimile, Alternaria solani,* and *Gibberella zeae*.

TABLE 1

| Fungal species | Disease control efficacy (average of two repeat experiments) |
|---|---|
| *Pythium dissimile* | 0 |
| *Alternaria solani* | 0 |
| *Botryotinia fuckeliana* | 99 |
| *Gibberella zeae* | 0 |

EXAMPLE 2

Ilicicolin H was also evaluated against several pathogens on leaf-piece assays at the rate of 100 ppm for *Uromyces viciae-fabae* on bean and *Zymoseptoria tritici* on wheat, and at the rate of 200 ppm for *Phytophthora infestans* on tomato. The compound was applied prior to inoculation with the pathogens.

| Test species | Host | Rate (ppm) |
|---|---|---|
| *Zymoseptoria tritici* | Wheat | 100 |
| *Phytophthora infestans* | Tomato | 200 |
| *Uromyces viciae-fabae* | Bean | 100 |

Mycelial growth or disease inhibition was assessed visually and scored using a 3 band system (0, 55 and 99 where 99 =total inhibition of hyphal growth/disease development, 55=partial inhibition, 0=no inhibition), 4 to 4 days after inoculation depending on the assay. Scores are given for numbered replicates, and average scores for the replicates (avg). Results are presented in Table 2. Ilicicolin H was active against *Phytophthora infestans* and *Zymoseptoria trici* and active in one rep against *Uromyces viciae-fabae*.

TABLE 2

| Fungal species | Disease control efficacy (average of two repeat experiments) |
|---|---|
| *Phytophthora infestans* (tomato) | 99 |
| *Zymoseptoria tritici* (wheat) | 99 |
| *Uromyces viciae-fabae* (bean) | 49 |

EXAMPLE 3

In order to test the effectiveness of Ilicicolin H on a variety of plant pathogens at different concentrations, leaf disks or leaf segments of various plant species were cut from plants grown in the greenhouse. The cut leaf disks or segments were placed in multi-well plates (24-well format) onto water agar. The leaf disks were sprayed with a test solution before (preventative) or after (curative) inoculation with the appropriate pathogen. Ilicicolin H was prepared as a DMSO solution (max. 10 mg/ml) which was diluted to the appropriate test concentration with 0.025% Tween 20 immediately before spraying. The inoculated leaf disks or segments were incubated under defined conditions (temperature, relative humidity, light, etc.) according to the respective test system. A single evaluation of disease level was carried out 3 to 9 days after inoculation (depending on the pathosystem) and percent disease control relative to the untreated check leaf disks or segments was then assessed. The results are shown in Tables 3 and 4 below. Ilicicolin H demonstrated activity against *Puccinia recondia*.

TABLE 3

| Pathogen | Host | Treatment timing |
|---|---|---|
| *Phytophthora infestans* | Tomato | Preventative |
| *Plasmopara viticola* | Grapevine | Preventative |
| *Blumeria graminis* f. sp. *tritici* (*Erysiphe graminis*) | Wheat | Preventative |
| *Puccinia recondita* | Wheat | Preventative |
| *Puccinia recondita* | Wheat | Curative |
| *Magnaporthe grisea* (*Pyricularia oryzae*) | Rice | Preventative |
| *Phaeosphaeria nodorum* (*Septoria nodorum*) | Wheat | Preventative |
| *Pyrenophora teres* | Barley | Preventative |
| *Alternaria solani* | Tomato | Preventative |

TABLE 4

| Fungal species | Leaf-piece test rates (200 ppm), efficacy | Leaf-piece test rates (60 ppm), efficacy | Leaf-piece test rates (20 ppm), efficacy |
|---|---|---|---|
| *Phytophthora infestans* (tomato-preventative) | 0 | 0 | 0 |
| *Plasmopara viticola* (grapevine-preventative) | 0 | 0 | 0 |
| *Blumeria graminis* f. sp. *tritici* (*Erysiphe graminis*) (wheat-preventative) | 0 | 0 | 0 |
| *Puccinia recondita* (wheat-preventative) | 90 | 50 | 0 |
| *Puccinia recondita* (wheat-curative) | 0 | 0 | 0 |
| *Phaeosphaeria nodorum* (*Septoria nodorum*) (wheat-preventative) | 0 | 0 | 0 |
| *Pyrenophora teres* (barley-preventative) | 0 | 0 | 0 |
| *Alternaria solani* (tomato-preventative) | 0 | 0 | 0 |
| *Magnaporthe grisea* (rice-preventative) | 0 | 0 | 0 |

EXAMPLE 4

Suspensions of mycelial fragments or conidia of a fungal species, prepared either freshly from liquid cultures of the fungus or from cryogenic storage, were directly mixed into nutrient broth. DMSO solutions of Ilicicolin H (max. 10 mg/ml) were diluted with 0.025% Tween 20 by a factor of 50, and 10µ L of this solution was pipetted into a microtitre plate (96-well format). The nutrient broth containing the fungal spores/mycelia fragments was then added to give a final concentration of Ilicicolin H. The test plates were incubated in the dark at 24° C. and 96% relative humidity. The inhibition of fungal growth was determined photometrically after 2-7 days, depending on the pathosystem, and percent antifungal activity relative to the untreated check was calculated. The results are shown in Tables 4 and 5 below. Ilicicolin H demonstrated activity against *Botryofinia funckeniana, Glomerella lagenanium, Mycosphaerella arachidis, Zymnoseptoria tritici, Gaeumanomyces graminis, Monographella nivalis, Thanalephorus cucumeis* and *Sclerotinia sclerotiorum*.

TABLE 4

| Pathogen |
|---|
| *Pythium ultimum* |
| *Botryotinia fuckeliana* (*Botrytis cinerea*) |
| *Glomerella lagenarium* (*Colletotrichum lagenarium*) |
| *Mycosphaerella arachidis* (*Cercospora arachidicola*) |
| *Zymoseptoria tritici* |
| *Gaeumannomyces graminis* |
| *Monographella nivalis* (*Microdochium nivale*) |
| *Fusarium culmorum* |
| *Thanatephorus cucumeris* (*Rhizoctonia solani*) |
| *Sclerotinia sclerotiorum* |

TABLE 5

| Fungal species | Liquid-culture test rates (20 ppm), efficacy | Liquid-culture test rates (2 ppm), efficacy | Liquid-culture test rates (0.2 ppm), efficacy |
| --- | --- | --- | --- |
| Pythium ultimum | 0 | 0 | 0 |
| Botryotinia fuckeliana (Botrytis cinerea) | 100 | 70 | 0 |
| Glomerella lagenarium (Colletotrichum lagenarium) | 100 | 50 | 0 |
| Mycosphaerella arachidis (Cercospora arachidicola) | 100 | 100 | 0 |
| Zymoseptoria tritici | 100 | 100 | 90 |
| Gaeumannomyces graminis | 100 | 90 | 0 |
| Monographella nivalis (Microdochium nivale) | 100 | 100 | 0 |
| Fusarium culmorum | 0 | 0 | 0 |
| Thanatephorus cucumeris (Rhizoctonia solani) | 70 | 50 | 0 |
| Sclerotinia sclerotiorum | 50 | 20 | 0 |

EXAMPLE 5

For the production of Ilicicolin H, *Cylindrocladium ilicicola* is grown and cultivated as described in Hayakawa et al., "Ilicicolins, antibiotics from *Cylindrocladium ilicicola*," *Journal of Antibiotics* 1971, 24, 653-4. *Gliocladium roseum* is grown and cultivated as described in Junker et al., "Scale-Up Studies on a Defined Medium Process for Pilot Plant Production of Illicicolin by *Gliocladium roseum*," *Biotechnology Progress* 2001, 17, 278-286. The fermentation broth from producer strains is lyophilized to remove water to afford a dry powder. The cells in the fermentation broth is broken if necessary by addition of organic solvent such as methanol, ethanol, acetone, and the like, and then evaporated to dryness to afford a powder. The fermentation broth obtained directly or after breaking the cells with solvent is sprayed onto the plant by foliar treatment, mixed with seeds, or used as a soil inoculant. In addition, broth powders generated using either of the two methods is mixed with appropriate agent(s) and sprayed by foliar treatment, mixed with seeds, or used as a soil inoculant.

Examples of Formulations of Ilicicolin H for Agricultural Use

Specific embodiments of a formulation of Ilicicolin H for use in agriculture are provided below. The final amounts (wt. %) of concentrate components are set forth in Table 6 below.

TABLE 6

| Ingredient | Function | Example A | Example B | Example C | Example D | Example E |
| --- | --- | --- | --- | --- | --- | --- |
| Tetrohydrofurfuryl alcohol | Solvent | 70.91 | 64.19 | 69.19 | 35.59 | 36.59 |
| Ethyl lactate | Solvent | 0 | 0 | 0 | 35.60 | 36.60 |
| Butyl ether derivative of EO/PO block copolymer (Toximul ® 8320) | Non-ionic surfactant | 0 | 3.00 | 0 | 0 | 0 |
| Tristyrylphenol ethoxylate with approximately 16 moles ethoxylation (Soprophor ® BSU) | Non-ionic surfactant | 11.10 | 8.50 | 0 | 11.00 | 11.00 |
| Polyethylene glycol dilaurate (PEG 400DL) | Non-ionic surfactant | 2.02 | 0 | 0 | 2.00 | 0 |
| Tristyrylphenol ethoxylate phosphate ester (Soprophor ® 3D33) | Anionic surfactant | 0 | 8.50 | 15.00 | 0 | 0 |
| Ilicicolin H technical (purity 97%) | Active ingredient | 5.92 | 5.86 | 5.86 | 5.86 | 5.86 |

While the invention has been described and illustrated in reference to specific embodiments thereof, those skilled in the art will appreciate that various changes, modifications, and substitutions can be made therein without departing from the spirit and scope of the invention. It is intended therefore that the invention be limited only by the scope of the claims which follow and that such claims be interpreted as broadly as is reasonable.

What is claimed is:

1. A method for treating or controlling a fungal infection on an agricultural product comprising the application to said agricultural product a composition comprising an agriculturally effective amount of Ilicicolin H and an agriculturally acceptable carrier and wherein said fungal infection is selected from the group consisting of *Botryotinia fuckeliana, Glomerella lagenarium, Mycosphaerella arachidis, Zymoseptoria tritici, Gaeumannomyces graminis, Monographella nivalis, Thanatephorus cucumeris, Sclerotinia sclerotiorum,* and *Puccinia recondita.*

2. The method according to claim 1 wherein said agricultural product is a plant or seed.

3. The method according to claim 1 wherein the application is directly to the agricultural product.

4. The method according to claim 3 wherein the application is by foliar spray.

* * * * *